United States Patent
Baumann et al.

(10) Patent No.: US 8,642,811 B2
(45) Date of Patent: Feb. 4, 2014

(54) PREPARATION OF PRIMARY DIAMINES HAVING A LINEAR MAIN CHAIN FOR POLYAMIDE SYNTHESES

(75) Inventors: Franz-Erich Baumann, Duelmen (DE); Matthias Ullrich, Marl (DE); Martin Roos, Haltern am See (DE); Peter Hannen, Herten (DE); Frank-Martin Petrat, Muenster (DE); Harald Haeger, Luedinghausen (DE); Angela Koeckritz, Berlin (DE); Guido Walther, Rostock (DE); Jens Deutsch, Rangsdorf (DE); Andreas Martin, Berlin (DE)

(73) Assignee: Evonik Degussa GmbH, Essen (DE)

( * ) Notice: Subject to any disclaimer, the term of this patent is extended or adjusted under 35 U.S.C. 154(b) by 106 days.

(21) Appl. No.: 13/364,493

(22) Filed: Feb. 2, 2012

(65) Prior Publication Data

US 2012/0203033 A1 Aug. 9, 2012

(30) Foreign Application Priority Data

Feb. 3, 2011 (DE) .......................... 10 2011 003 595

(51) Int. Cl.
*C07C 209/16* (2006.01)

(52) U.S. Cl.
USPC ........................................ 564/480

(58) Field of Classification Search
None
See application file for complete search history.

(56) References Cited

U.S. PATENT DOCUMENTS

| | | | | |
|---|---|---|---|---|
| 2,754,330 A | * | 7/1956 | Schreyer | 564/480 |
| 4,745,190 A | * | 5/1988 | Marsella | 544/170 |
| 2011/0152525 A1 | | 6/2011 | Milstein et al. | |
| 2012/0232292 A1 | * | 9/2012 | Schaub et al. | 549/492 |
| 2012/0232293 A1 | * | 9/2012 | Schaub et al. | 549/492 |
| 2012/0232294 A1 | * | 9/2012 | Schaub et al. | 549/495 |
| 2012/0232309 A1 | * | 9/2012 | Schaub et al. | 564/474 |

FOREIGN PATENT DOCUMENTS

| | | |
|---|---|---|
| GB | 1195287 | 6/1970 |
| WO | WO 2010/018570 A1 | 2/2010 |

OTHER PUBLICATIONS

Extended European Search Report issued Jun. 29, 2012 in Patent Application No. 12150709.9 with English Translation of Category of Cited Documents.

* cited by examiner

*Primary Examiner* — Brian J Davis
(74) *Attorney, Agent, or Firm* — Oblon, Spivak, McClelland, Maier & Neustadt, L.L.P.

(57) ABSTRACT

The invention provides a method to produce primary diamines by catalytic conversion of diols having a linear main chain of from 4 to 31 carbon atoms into the corresponding diamines. The reaction is conducted in a liquid or supercritical phase and is catalyzed by a homogeneous ruthenium-containing complex. The primary diamines obtained may be suitable for polyamide syntheses.

20 Claims, No Drawings

PREPARATION OF PRIMARY DIAMINES HAVING A LINEAR MAIN CHAIN FOR POLYAMIDE SYNTHESES

CROSS REFERENCE TO RELATED APPLICATIONS

This application claims priority to German Patent Application No. 102011003595.8, filed Feb. 3, 2011, the enclosure of which is incorporated herein in its entirety by reference.

BACKGROUND OF THE INVENTION

A number of processes in the liquid, gaseous or supercritical phase have been described in science and industry for the conversion of alcohols by reaction with ammonia into primary amines.

The challenge for these processes is to achieve high selectivities to the primary amine. Since alkylamines are more nucleophilic than ammonia and their nucleophilicity increases with the number of alkyl groups on the nitrogen atoms, secondary and tertiary linear amines are preferentially formed. In addition, a limited selectivity to the diamine has been observed when diols are used as starting material in such reactions because appreciable amounts of intermediate amino alcohol have frequently also been isolated. In the case of relatively short-chain diols, cyclization as alternative reaction also plays a significant role (e.g. Fischer et al., Catal. Today 1997, 37, 167-189).

The reaction in the gas phase is possible for readily vaporizable lower alcohols and diols. It is carried out over heterogeneous catalysts in the presence of $NH_3$ and $H_2$. The high temperatures of up to 400° C. and pressures of up to 300 bar which are necessary frequently bring about the formation of undesirable intermediates, by-products and subsequent products, e.g. secondary and tertiary amines, alkenes and alkanes (by means of dehydration/hydrogenation), cyclic species and in the case of diols also amino alcohols. Direct aminations over heterogeneous catalysts have also been carried out in the liquid phase; in some cases, it is difficult to distinguish between gas and liquid phase on the basis of the available data. Examples of the reaction over heterogeneous catalysts are the patents and literature references mentioned below.

Thus, EP 0963975 describes the direct amination of, inter alia, primary alcohols and 1,2- to 1,6-diols over oxidic $ZrO_2$-supported Cu—Ni—Co catalysts in the presence of hydrogen. Depending on the reaction conditions, amino alcohols, cyclic compounds or diamines can be obtained, with the diamine selectivities described being low. In DE 1543377, $C_4$-$C_8$-diols are hydrogenatively aminated to the diamines over Co—Cr—Mn catalysts in the presence of $P_4O_{10}$, sometimes under hydrogen pressures of up to 300 bar. In this way, 86.5% of hexamethylenediamine can be prepared from 1,6-hexanediol in a single pass. DE 102006061045 (over Ni—Cu/$ZrO_2$ catalysts) and DE 102006061042 (over Ni—Cu—Ru/$ZrO_2$ catalysts) describe the hydrogenative amination of alcohols or dihydroxy and polyhydroxy compounds in the range from 180° C. to 220-250° C., but preferably of stearyl alcohols.

WO 9638226 describes the direct hydrogenative amination of, inter alia, C2-C6-alcohols and -diols, also those having further functional groups, by means of ammonia over Re—Cu—Ni—Co catalysts and/or Ru catalysts. WO 2007093514 and WO 2007093552 describe the hydrogenative amination of ethylene glycol over Ru—Co catalysts; ethylenediamine was isolated in yields of up to 57% together with further products. In the examples, only monoethanolamine is used as substrate. Cyclohexanol is reacted with $NH_3$ and 200 bar of $H_2$ at 260-300° C. over Ca aluminosilicates to form cyclohexylamine. The preparation of various primary monoamines is described in DE 19859776 (over Cu—CuO/$TiO_2$ catalysts), WO 2008072428 (over Ru/$ZrO_2$ catalysts) and WO 2007077903 (over Ru/$Al_2O_3$ catalysts) at reaction temperatures of 180-250° C.

Various diether or polyether diols have likewise been subjected to direct hydrogenative aminations using ammonia. DE 3903367 describes the amination of diethylene glycol over oxidic Zr—Cu—Ni—Co catalysts, giving aminoethoxyethanol and morpholine as main products. Polyether diols are hydrogenatively aminated directly over Raney Ni or Raney Co catalysts at 220-250° C., with 0.06-0.12% of higher amines being formed. The preparation of polyetheramines in U.S. Pat. No. 4,153,581 is carried out at 140° C. over Co—Cu catalysts which contain Zn, Zr or Fe as further active components; here, the proportion of aminated products in the reaction mixture is only 12-60 percent by weight.

Baiker and coworkers have published a study on the continuous direct amination of propanediol in supercritical ammonia (Angew. Chem. Int. Ed. 1999, 38, 351-354). Here too, the problems of the selectivity to the diamine, which does not exceed 20%, are discussed.

The additional use of hydrogen in a hydrogenative amination in which the use of heterogeneous catalysts is necessary is costly. Such processes are not suitable for relatively long-chain linear aliphatic alcohols and diols because the at least partial decomposition of starting material and product under the reaction conditions required would make the economics questionable. In addition, the achievable selectivities to the diamine are not competitive for applications in the polyamide field.

Only very few examples of the homogeneously catalysed direct amination of primary and secondary alcohols in liquid phase are conventionally known. Here, the use of ruthenium catalysts permits the concept of "borrowing hydrogen" (Williams et al. Adv. Synth. Catal. 2007, 349, 1555-1575), i.e. hydrogen does not have to be additionally introduced since the $H_2$ equivalent which is initially liberated during the dehydrogenation of the alcohol in the first reaction step is "parked" on the catalyst and is reintroduced into the cycle in a later phase. Milstein and coworkers (Angew. Chem. Int. Ed. 2008, 47, 8661-8664) report the selective reaction of monohydric, including functionalized, alcohols in the liquid phase in the presence of excess ammonia and the ruthenium-PNP pincer complex carbonylchloro[4,5-bis-(diisopropylphosphinomethyl)acridine]hydridoruthenium(II). The yields of primary amine were 78-96%. The reactions were carried out in a solvent at 7.5 bar, 135-180° C. over a period of 12-36 hours. Polyhydric alcohols were not aminated, nor were secondary alcohols. In addition, WO 2010018570 also describes the use of quinolinyl-based PNP pincer ligands, with comparable results.

Beller and coworkers (Angew. Chem. 2010, 122, 8303) and Vogt and coworkers (Angew. Chem. 2010, 122, 8307) both describe the preparation of primary amines from secondary alcohols in yields of up to 93% using a catalyst prepared in situ from the Ru and P(III) precursor compounds dodecacarbonyltriruthenium(0) and 2-(dicyclohexylphosphino)-1-phenyl-1H-pyrrole (cataCXium®PCy). Here too, no diols were used as starting materials.

It cannot be assumed from the abovementioned patent documents and literature references that the catalytic processes described can be applied in the same way to polyhydric alcohols. The abovementioned secondary reactions can play a selectivity-limiting role; in addition, oligomerizations via amino alcohols formed as intermediates are possible in the liquid phase.

BRIEF SUMMARY OF THE INVENTION

It is therefore an object of the present invention to provide a single-stage process which gives primary amines having a linear main chain. The advantage of such a process over the prior art would be the direct selective production of such diamines in a high purity which would allow, after an optional further, simple purification step, direct use of the diamines in the production of polyamides, resulting in a substantial technical simplification of such a process.

This and other objectives have been achieved by the present invention, which in a first embodiment provides a method for preparing a primary diamine, comprising: reacting at least one diol having a linear main chain with at least one of ammonia and an ammonia-liberating compound in a liquid or supercritical phase in the presence of a homogeneous ruthenium catalyst to obtain the primary diamine; wherein the main chain of the primary diamine is the linear main chain of the diol.

In a preferred embodiment, the linear main chain of the diol comprises from 4 to 31 carbon atoms.

In another preferred embodiment, the homogeneous ruthenium catalyst comprises a ruthenium-ligand complex having at least one P(III) group.

In further embodiments of the invention the homogeneous ruthenium catalyst may be preformed from a Ru precursor compound prior to the reaction or formed from a Ru precursor compound in situ in the reaction; wherein the Ru precursor compound is at least one selected from the group consisting of ruthenium(III) chloride, ruthenium(III) acetate, ruthenium (III) acetylacetonate, dodecacarbonyltriruthenium(0), carbonylchlorohydridotris-(triphenylphosphane)ruthenium(II) and di-μchlorobis[chloro(p-cymene)ruthenium(II)].

In a highly preferred embodiment of the present invention, the homogeneous ruthenium catalyst comprises at least one ligand selected from the group consisting of a tridentate pincer ligand, a monodentate phosphane and a bidentate phosphane and in a further highly preferred embodiment, the catalyst is carbonylchloro[4,5-bis(diisopropyl-phosphinomethyl)acridine]-hydridoruthenium(II).

DETAILED DESCRIPTION OF THE INVENTION

The present invention provides a process for preparing primary diamines having a linear main chain from the corresponding diols by reaction with ammonia and/or an ammonia-liberating compound or mixtures thereof in a liquid or supercritical phase in the presence of a homogeneous ruthenium catalyst. The process of the invention preferably provides for the direct reaction of one or more diols having a linear main chain and from 4 to 31 carbon atoms, preferably having a main chain of C5 to C31, and particularly preferably having a main chain of from C6 to C31, with ammonia and/or an ammonia-liberating compound or mixtures thereof as nitrogen source by the method of "borrowing hydrogen", i.e. without an additional external hydrogen source. Without describing a limiting recitation, equation 1 shows a general scheme of the reaction according to the present invention for straight-chain, α,ω-diols with ammonia. Primary diamines which have a linear main chain and are suitable for use as monomers in the production of polyamides may in this way be synthesized directly from the diols.

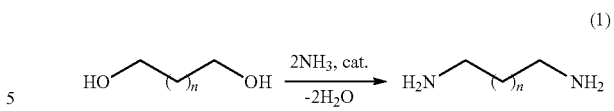

For the purposes of the present invention, "diols having a linear main chain" are diols of the formula (I), $$R^1CH(OH)-X-CH(OH)R^2 \tag{I}$$

where $R^1$ and $R^2$ are each, independently, hydrogen or substituents having 1-7 carbon atoms, preferably hydrogen or alkyl groups having 1-7 carbon atoms, more preferably hydrogen or methyl, and the unit X is a saturated or unsaturated organic radical which may comprise elements of the boron, carbon, nitrogen and oxygen groups of the Periodic Table (main groups 3-6 of the Periodic Table), particularly preferably the elements carbon, nitrogen and oxygen. X is preferably a carbon main chain unit having n methylene units ($-CH_2$-groups), i.e. the diols are diols of the formula (II), $$R^1CH(OH)-(CH_2)_n-CH(OH)R^2 \tag{II}$$

where $R^1$ and $R^2$ each have, independently the above meanings, in particular hydrogen or methyl, and n is 0-29, preferably n is 1-29 and particularly preferably n is 2-29.

Very particular preference is given to straight-chain diols of the formula (III), $$HO-CH_2-(CH_2)_n-CH_2-OH \tag{III}$$

where n=2-29, preferably n=3-29 and particularly preferably n=4-29.

Advantages of the process of the invention may be the avoidance of multistage processes and the formation of coproducts. No intermediate isolation and purification may be required. It is possible to use heat-sensitive substrates, for example ones based on renewable raw materials. This may make it possible to obtain new diamine components for the synthesis of high-quality polyamides, which components have previously not been available or not been available in this quality.

The process of the invention for preparing primary diamines having a linear main chain preferably comprises:

I. charging to a reaction vessel the at least one diol having a linear main chain, optionally with mixing-in of the homogeneous ruthenium catalyst or precursor compounds of the homogeneous ruthenium catalyst;

II. adding the at least one of ammonia and an ammonia-liberating compound, optionally, with mixing-in of the homogeneous ruthenium catalyst or precursor compounds of the homogeneous ruthenium catalyst;

III. establishing required reaction conditions of the reaction vessel and conducting the reaction to obtain the primary diamine;

IV. optionally isolating the primary diamine; and

V. optionally purifying the primary diamine;

wherein the homogeneous ruthenium catalyst or precursor compounds of the homogeneous ruthenium catalyst is included in at least one of I and II.

Suitable reaction vessels for carrying out the reactions may be, for example, all conventional types of autoclaves and also all conventional types of apparatuses which operate according to the principle of cocurrent or countercurrent material flow, such as for instance, tube reactors. Depending on the specific medium and/or depending on the specific conditions of the respective reaction, the reactor may be operated under atmospheric pressure or under pressures of 1-1000 bar, preferably 5-500 bar and particularly preferably 5-100 bar. This pressure may be generated by injected ammonia and/or by pressurization of the reactor with a further, preferably inert gas such as nitrogen or argon and/or by formation of ammonia in situ from an ammonia-liberating compound or mixtures thereof and/or by setting of the desired reaction temperature.

The catalysts used in process step II. in the process of the invention may preferably be ruthenium catalysts, in particular ruthenium-ligand complexes having at least one P(III) group. Thus, the catalysts mentioned preferably may contain, ligands having at least one function which comprises trivalent phosphorus and is capable of coordination, for example phosphane functions. Particular preference may be given to using tridentate pincer ligands which contain not only groups comprising trivalent phosphorus but also structural elements which can likewise coordinate to the ruthenium. These may be based on elements of the boron, carbon, nitrogen and oxygen groups of the Periodic Table (main groups 3-6 of the Periodic Table). Preferred coordinating groups may be C, N or O donors.

To prepare the catalysts used in III. in the process of the invention, it may be possible, to add ruthenium in the form of precursor compounds. These are ruthenium salts or ruthenium complexes in which weakly coordinated ligands may be easily replaced in situ by P(III) groups and/or by groups based on elements of the boron, carbon, nitrogen and oxygen groups of the Periodic Table, preferably C, N or O donors, during a possible preforming of the catalyst or during combining of the ruthenium component and the ligand component. Examples of such ruthenium precursor compounds of the ruthenium catalyst may be ruthenium(III) chloride, ruthenium(III) acetate, ruthenium(III) acetylacetonate, dodecacarbonyltriruthenium(0), carbonylchlorohydridotris(triphenylphosphane)ruthenium(II) or di-μ-chlorobis[chloro(p-cymene)ruthenium(II)].

Preferred catalysts for the process may be ruthenium complexes having tridentate pincer ligands or ruthenium complexes having monodentate or bidentate phosphanes. These may be produced, analogously to the abovementioned procedure, in situ from corresponding suitable precursors as mixtures in which they are present. It likewise may be possible to use ruthenium-ligand complexes which have previously been isolated as such by appropriate methods by a person skilled in the art as catalysts for this purpose. Particularly preferred catalysts which may be mentioned by way of example, are ruthenium complexes having tridentate pincer ligands, in particular carbonylchloro[4,5-bis(diisopropylphosphinomethyl)acridine]hydridoruthenium(II), or ruthenium complexes having a monodentate or bidentate phosphane, or a complex prepared in situ from dodecacarbonyltriruthenium(0) and the phosphane 2-(dicyclohexylphosphino)-1-phenyl-1H-pyrrole (cataCXium®PCy).

As preferred amount of the ruthenium catalyst or the corresponding Ru- and P(III)-containing precursor compounds, an amount, based on the diol, in the range 0.01-20 mol %, preferably in the range 0.01-6 mol % and particularly preferably in the range 0.25-6 mol %, may be added.

As preferred ratio of Ru to P(III) groups in catalysts prepared beforehand in isolated form or prepared in situ from corresponding suitable precursor compounds or mixtures in which they are present, a molar ratio in the range 1:1-1:20, preferably in the range 1:2-1:6 and particularly preferably in the range 1:2-1:3 may be selected in the case of ruthenium complexes having tridentate pincer ligands or bidentate phosphanes; while in the case of ruthenium complexes having monodentate phosphanes the preferred molar ratio may be in the range 1:1-1:20, preferably in the range 1:1-1:6, and particularly preferably in the range 1:1-1:2.

In the process of the invention, ammonia and/or an ammonia-liberating compound or mixtures thereof may be added. Examples of such compounds may be urea, uric acid, ammonium salts and derivatives of a primary amide, for example, symmetrical and unsymmetrical carbamates, carbaminates, semicarbazides and semicarbazoles and also aminium salts or organic or inorganic esters of all these. Preference may be given to using ammonia itself, with liquid or gaseous ammonia being able to be used in this embodiment.

As preferred molar ratio of the sum of the hydroxy functions of the one or more diols to the equivalents of ammonia, which may be formed from the ammonia introduced and/or the ammonia-liberating compound or the sum of such compounds, a value in the range 1:2-1:5000, preferably in the range 1:10-1:1000 and particularly preferably 1:20-1:500, may be set.

As preferred reaction temperature in process step III. of the process of the invention, a temperature in the range 60-220° C., preferably in the range 90-180° C. and particularly preferably in the range 125-165° C., may be set.

As preferred pressure during the reaction in the process of the invention, a pressure in the range 1-1000 bar, preferably 5-500 bar and particularly preferably 5-100 bar, may be set. This pressure may be generated by means of the injected ammonia and/or by pressurizing the reactor with a further, preferably inert gas such as nitrogen or argon and/or by means of ammonia formed in situ from an ammonia-liberating compound or mixtures thereof and/or by setting the desired reaction temperature.

As preferred concentration of the diol or diols used in a solvent or a supercritical medium during the reaction in the process of the invention, a concentration in the range 0.1-10 000 mmol/l, preferably in the range 5-1000 mmol/l and particularly preferably in the range 10-500 mmol/l, may be set. As supercritical medium, preference may be given to using supercritical ammonia.

It may be possible to use solvents or solvent mixtures. Organic solvents selected from the group consisting of tertiary and neopentylic alcohols, ethers, arenes and aliphatics may preferably be used. Particular preference may be given to using tert-butanol, 2-methyl-2-butanol, toluene, xylene, mesitylene, dioxane, tetrahydrofuran, cyclohexane, methyl tert-butyl ether and anisole or mixtures thereof. There may be no particular requirements regarding the purity of the solvents.

The diamines having a linear main chain which are formed may be optionally be isolated and purified. For example, the reaction mixture obtained may be filtered and subjected to a distillation in order to isolate the diamine or diamines formed. Further purification methods known to those skilled in the art may likewise be possible. For example, it may be possible to feed a primary diamine having a linear main chain which has been prepared by the reaction according to the invention after purification or directly to a subsequent polycondensation by preparing the diaminium dioate ("nylon salt") to be used in this polycondensation in situ by addition of an approximately stoichiometric amount of the appropriate dicarboxylic acid, purifying or isolating it by methods known to those skilled in the art and subsequently using it in the polycondensation.

Having generally described the invention, a further understanding may be obtained by reference to certain specific examples which are provided herein for purposes of illustration only, and are not intended to be limiting, unless otherwise specified.

Example 1

Reaction of 1,19-nonadecanediol 3.01 g (10.0 mmol) of 1,19-nonadecanediol and 151 mg (0.25 mol %) of carbonylchloro[4,5-bis(diisopropylphosphinomethyl)acridine]hydridoruthenium(II) were dissolved under protective gas in 25 ml of 2-methyl-2-butanol and transferred to an autoclave provided with stirrer, heating and temperature measuring facility. 6 ml of liquid ammonia were subsequently introduced into the autoclave by means of a spindle press. The autoclave was closed and the contents stirred at 140° C. for 48 hours. This resulted in an increase in the internal pressure from 22 to 40 bar. After cooling, the contents of the reactor were filtered through kieselguhr, the filtrate was evaporated to dryness and the residue subjected to a bulb tube distillation. Yield of linear primary diamine: 2.02 g (68% of theory; $bp_{0.8\ mbar}$=170-185° C.), conversion of the linear diol: >99%.

Example 2

Reaction of 1,12-dodecanediol

Reaction and work-up were carried out under the same conditions as in Example 1 using 10.0 mmol of 1,12-dodecanediol. Yield of linear primary diamine: 1.36 g (68% of theory; $bp_{0.8\ mbar}$=115-125° C.), conversion of the linear diol: >99%.

Example 3

Reaction of 1,8-octanediol

The reaction was carried out under the same conditions as in Example 1 using 10.0 mmol of 1,8-octanediol. Yield and conversion were determined by gas chromatography using commercially available reference compounds. Yield of linear primary diamine: 78%, conversion of the linear diol: >99%.

Example 4

Reaction of 1,6-hexanediol

The reaction was carried out under the same conditions as in Example 1 using 10.0 mmol of 1,6-hexanediol. Yield and conversion were determined by gas chromatography using commercially available reference compounds. Yield of linear primary diamine: 55%, conversion of the linear diol: >99%.

Example 5

Reaction of 1,8-octanediol

A mixture of 10.0 mmol of 1,8-octanediol, 12 mol % of 2-(dicyclohexylphosphino)-1-phenyl-1H-pyrrole (cataCXium®PCy) and 4 mol % of $Ru_3(CO)_{12}$ was dissolved under protective gas in 25 ml of 2-methyl-2-butanol and transferred to an autoclave provided with stirrer, heating and temperature measuring facility. 6 ml of liquid ammonia were subsequently introduced into the autoclave by means of a spindle press. The autoclave was closed and the contents stirred at 170° C. for 48 hours. This resulted in an increase in the internal pressure from 22 to 40 bar. After cooling, the contents of the reactor were filtered through kieselguhr. Yield and conversion were determined by gas chromatography using commercially available reference compounds. Yield of linear primary diamine: 17%, conversion of the linear diol: 96%.

The invention claimed is:

1. A method for preparing a primary diamine, comprising:
reacting, in a reactor, at least one diol comprising a linear main chain with at least one of ammonia and an ammonia-liberating compound in a liquid or supercritical phase in the presence of a homogeneous ruthenium catalyst to obtain the primary diamine;
wherein the primary diamine comprises a main chain, which is the linear main chain of the diol.

2. The method according to claim 1, wherein the linear main chain comprises from 4 to 31 carbon atoms.

3. The method according to claim 1, wherein the homogeneous ruthenium catalyst comprises a ruthenium-ligand complex comprising at least one P(III) group.

4. The method according to claim 3, further comprising:
preforming the ruthenium-ligand complex from a Ru precursor compound prior to said reacting or forming the ruthenium-ligand complex from a Ru precursor compound in situ in said reacting;
wherein the Ru precursor compound is at least one selected from the group consisting of ruthenium(III) chloride, ruthenium(III) acetate, ruthenium(III) acetylacetonate, dodecacarbonyltriruthenium(0), carbonylchlorohydridotris(triphenylphosphane)ruthenium(II) and di-µ-chlorobis[chloro(p-cymene)ruthenium(II)].

5. The method according to claim 3, wherein the homogeneous ruthenium catalyst comprises at least one ligand selected from the group consisting of a tridentate pincer ligand, a monodentate phosphane and a bidentate phosphane.

6. The method according to claim 5, wherein the homogeneous ruthenium catalyst comprises a tridentate pincer ligand and the catalyst is carbonylchloro[4,5-bis(diisopropyl-phosphinomethyl)acridine]hydridoruthenium(II).

7. The method according to claim 5, wherein the homogeneous ruthenium catalyst comprises a bidentate phosphane which is prepared in situ from dodecacarbonyltriruthenium (0) and 2-(dicyclohexylphosphino)-1-phenyl-1H-pyrrole.

8. The method according to claim 1, further comprising:
prior to said reacting,
charging to the reactor the at least one diol comprising a linear main chain, optionally with mixing-in of the homogeneous ruthenium catalyst or precursor compounds of the homogeneous ruthenium catalyst; and
adding the at least one of ammonia and an ammonia-liberating compound, optionally, with mixing-in of the homogeneous ruthenium catalyst or precursor compounds of the homogeneous ruthenium catalyst; and
after said reacting,
optionally isolating the primary diamine; and
optionally purifying the primary diamine;
wherein
the homogeneous ruthenium catalyst or precursor compounds of the homogeneous ruthenium catalyst is included in at least one of said charging and said adding, and
said charging comprises at least one selected from the group consisting of a) charging as a fluid phase by dissolution or suspension in a solvent or solvent mixture; b) charging as a fluid phase by melting of the diol; and c) dry charging the diol as a solid phase.

9. The method according to claim 8, wherein a reaction temperature is from 60 to 220° C.

10. The method according to claim 1, wherein ammonia is reacted and the ammonia is liquid or gaseous ammonia.

11. The method according to claim 1, wherein a molar ratio of a sum of hydroxy functional groups of the at least one diol to equivalents of ammonia in said reacting is from 1:2 to 1:5000.

12. The method according to claim 1, wherein a pressure of said reacting is from 1 to 1000 bar.

13. The method according to claim 12, wherein the pressure is controlled by at least one method selected from the group consisting of adding ammonia into the reactor, forming ammonia in situ from an ammonia-liberating compound, adding an inert gas, and setting a reaction temperature.

14. The method according to claim 8, wherein the at least one diol is charged as a solution or suspension in at least one organic solvent selected from the group consisting of a tertiary and neopentylic alcohol, an ether, an arene, and an aliphatic.

15. The method according to claim 14, wherein the organic solvent is at least one selected from the group consisting of tert-butanol, 2-methyl-2-butanol, toluene, xylene, mesitylene, dioxane, tetrahydrofuran, cyclohexane, methyl tert-butyl ether and anisole.

16. The method according to claim 1, wherein the at least one diol comprising a linear main chain is of formula (I):

$$R^1CH(OH)-X-CH(OH)R^2 \quad (I)$$

wherein

R$^1$ and R$^2$ are each, independently, hydrogen or an alkyl group comprising 1-7 carbon atoms, and X is a saturated or unsaturated organic radical optionally comprising boron, carbon, nitrogen or oxygen.

17. The method according to claim 16, wherein the at least one diol of formula (I) is of formula (II):

$$R^1CH(OH)-(CH_2)_n-CH(OH)R^2 \quad (II)$$

wherein R$^1$ and R$^2$ are each, independently, hydrogen or an alkyl group having comprising 1-7 carbon atoms and n is an integer of from 0 to 29.

18. The method according to claim 17, wherein the at least one diol of formula (II) is of formula (III):

$$HO-CH_2-(CH_2)_n-CH_2-OH \quad (III)$$

wherein n is an integer of from 2 to 29.

19. The method according to claim 1, wherein a concentration of the at least one diol is from 0.1 to 10.000 mmol/l.

20. The method according to claim 1, wherein said reacting is conducted in a supercritical phase which comprises supercritical ammonia.

* * * * *